United States Patent [19]

Aoyagi et al.

[11] 4,453,940
[45] Jun. 12, 1984

[54] AUTOCLAVABLE MEDICINAL-CONTAINING BAG FROM ETHYLENE-VINYL ACETATE COPOLYMER

[75] Inventors: Juuro Aoyagi; Toshizi Ichikawa, both of Tokyo, Japan

[73] Assignee: Terumo Corporation, Tokyo, Japan

[21] Appl. No.: 276,501

[22] Filed: Jun. 23, 1981

Related U.S. Application Data

[63] Continuation of Ser. No. 865,443, Dec. 29, 1977, abandoned.

[30] Foreign Application Priority Data

Jan. 8, 1977 [JP] Japan ................................. 52-1093

[51] Int. Cl.³ ...................... C08J 7/10; C08F 210/00; C08F 214/00; A61J 1/00
[52] U.S. Cl. ................. 604/408; 204/159.14; 128/DIG. 24; 206/524.6; 206/828
[58] Field of Search ............... 204/159.14; 128/214 D, 128/DIG. 24; 604/408

[56] References Cited

U.S. PATENT DOCUMENTS

| | | | |
|---|---|---|---|
| 3,022,543 | 2/1962 | Baird et al. | 204/159.14 |
| 3,160,575 | 12/1964 | Bartl et al. | 204/159.14 |
| 3,274,086 | 9/1966 | Potts | 204/159.14 |
| 3,530,084 | 9/1970 | Potts | 204/159.14 |
| 3,576,650 | 4/1971 | Underwood et al. | 128/272 |
| 3,734,843 | 5/1973 | Tubbs | 204/159.14 |
| 3,884,786 | 5/1975 | Domine et al. | 204/159.14 |
| 3,942,529 | 3/1976 | Waage | 128/272 |
| 3,953,557 | 4/1976 | Brax et al. | 204/159.14 |
| 4,044,187 | 8/1977 | Kremkau | 204/159.14 |
| 4,064,296 | 12/1977 | Bornstein et al. | 428/516 |
| 4,112,989 | 9/1978 | Grode et al. | 428/35 |
| 4,178,401 | 12/1979 | Weinberg et al. | 428/520 |

*Primary Examiner*—Melvin I. Marquis
*Assistant Examiner*—A. H. Koeckert
*Attorney, Agent, or Firm*—Bacon & Thomas

[57] ABSTRACT

A medical utensil having a portion to contact body fluid or liquid medicine is provided in which at least the contact portion is formed of a copolymer cross-linked by electron beam irradiation and/or γ-ray irradiation.

13 Claims, 6 Drawing Figures

AUTOCLAVABLE MEDICINAL-CONTAINING BAG FROM ETHYLENE-VINYL ACETATE COPOLYMER

This application is a continuation of application Ser. No. 865,443 filed Dec. 29, 1977 now abandoned.

BACKGROUND OF THE INVENTION (I) Field of the Invention:

The present invention relates to a medical utensil and more particularly to one in which the portion which contacts body fluid or liquid medicine is formed of synthetic resin.

(II) Description of the Prior Art

In the medical field, synthetic resins are used to form medical utensils requiring transparency or flexibility such as blood bags, fluid supply bags, catheters, tubes and the like. Known synthetic resins for such use are polyvinyl chloride or a blend of polyvinyl chloride with polyurethane, polybutadiene or polyacrylonitrile, and the like. Unfortunately, these conventional synthetic resins fail to completely satisfy the requirements for the medical utensil.

The requirements for the material of medical utensil are: (1) The material must not be attacked by body fluid or liquid medicine contacting it; (2) It must have a low permeability of water vapor or other gases; (3) It must have high heat-resistance since it is subjected to a high vapor pressure sterilization. In addition, it must have a high fusibility by heating, particularly high frequency heating, from a molding view point.

Polyvinyl chloride which is currently most widely used for the medical utensil material contains a plasticizer for imparting flexibility, a heat stabilizer for imparting heat stability, lubricant for improving the molding characteristic, and the like. When it contacts body fluid or liquid medicine, these additive agents are likely to elute from the material. This is undesirable in medical utensils. This material also has a low heat-resistance. Also, the above-mentioned blends are unsatisfactory in flexibility, transparency, and compatibility. In addition they exhibit poor heat-resistance.

Further, the above-mentioned synthetic resins have a relatively high permeability to vapor or gases. Accordingly, liquid medicine in the container made of such resins tends to change its composition due to vapor and its quality due to oxidation.

SUMMARY OF THE INVENTION

Accordingly, an object of the present invention is to provide a medical utensil which exhibits excellent flexibility and heat-resistance and is highly resistive to body fluid or liquid medicine, and low in gas permeability.

According to the present invention, there is provided a medical utensil including a portion designed to contact body fluid and/or liquid medicine, at least said portion being formed of a copolymer cross-linked at the degree of cross-linking of 20 to 75% by electron beam irradiation and/or γ-ray irradiation wherein said copolymer is represented by the formula:

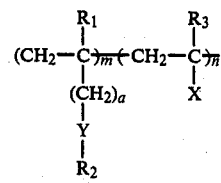

Formula I where each of $R_1$, $R_2$ and $R_3$ is, independently, hydrogen or a lower alkyl group having 1 to 5 carbon atoms; X is hydrogen, chlorine, or bromine; Y is

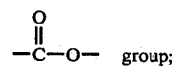

group;

$a$ is 0 or 1; m and n are an integer indicating the numbers of the corresponding units, respectively; and $m/m+n$ is 0.15 to 0.5.

BRIEF DESCRIPTION OF THE DRAWINGS

The present invention will be more fully understood from the following description when taken in connection with the accompanying drawings, in which.

DETAILED DESCRIPTION OF THE PREFERRED EMBODIMENTS

Figure 1:
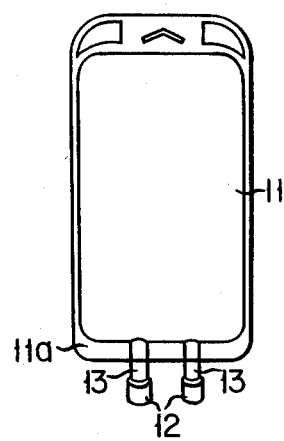
FIG. 1 shows a plan view of a fluid supply bag which is one of medical utensils according to the present invention.

As noted previously, a medical utensil according to the present invention has a portion which is to contact body fluid and/or liquid medicine and at least said portion is formed of a cross-linked copolymer of the formula I. The copolymer of the formula I may be prepared by polymerizing through a known radical polymerization technique at least one kind of ester having an acrylic group represented by a general formula

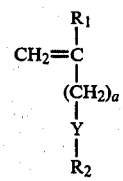

Formula II where $R_1$, $R_2$, Y and $a$ are as defined above and at least one kind of ethylene compound represented by a general formula

Formula III where $R_3$ and X are as defined above.

In the formulae I and II, a is 0 or 1 which indicates the absence of presence of methylene group, as mentioned above. When a is 0,

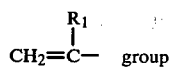 group and Y group are directly bonded together. Y is

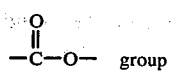 group and this does not limit the bonding with the $R_2$ radical. That is, a group $-Y-R_2$ indicates two groups

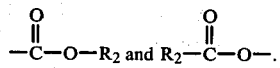.

Ester of the formula II includes vinyl acetate, allyl acetate, methyl acrylate, methyl metacrylate, ethyl acrylate, ethyl metacrylate, propyl acrylate, propyl metacrylate, n-butyl acrylate, n-butyl metacrylate, isobutyl metacrylate, diethylhexyl acrylate and the like. Vinyl acetate, butyl acrylate, and diethylhexyl acrylate are particularly preferable.

Examples of the compound of the formula III are ethylene, propylene, vinyl chloride, vinyl bromide, butene, pentene and the like. Preferred are ethylene, vinyl chloride, and vinyl bromide.

In the formula I, m and n represent the number of the unit derived from the monomer of the formula II and the number of the unit derived from the monomer of the formula III, respectively. Generally, the number of the unit derived from the monomer of the formula II occupies 15 to 50% of the total of the numbers of the entire units in the copolymer of the formula I and the remaining 85 to 50% are occupied by the number of the unit derived from the monomer of the formula III. That is, $m/m+n$ is 0.15 to 0.5. As will be referred to later, if the $m/m+n$ is less than 0.15, the heat fusibility of the resultant copolymer after cross-linking becomes poor. If it exceeds 0.5, the moldability of the resultant copolymer is lowered. Preferably it ranges from 0.2 to 0.45. Particularly preferred is ethylene-vinyl acetate copolymer including 15 to 30% of vinyl acetate unit and 70 to 85% of ethylene unit.

The term "copolymer" is used in the present specification and claims includes alternate polymer and block polymer as well as copolymer, terpolymer, etc.

Generally, the copolymer of the present invention has a molecular weight which is enough to enable it to be formed into a sheet, and has a weight average molecular weight ranging from about 10,000 to 250,000.

As described above, the medical utensil of the invention is made of a copolymer which is cross-linked at a degree between cross-linking of 20 to 75% by irradiating with γ-rays and/or electron beam. The irradiation for cross-linking the copolymer may be carried out at several steps in the manufacturing process of the medical utensil.

In a first embodiment, a desired medical utensil molding, for example, a blood bag molding or a catheter molding is manufactured by using noncross-linked copolymer of formula I in a suitable manner such as heat fusing, blow molding, etc. Then, the molding is irradiated with γ-rays and/or electron beam to attain a desired degree of cross-linking.

In a second embodiment, a powder or pellet of the noncross-linked copolymer is irradiated to some degree with electron beam and/or γ-rays attaining a degree of cross-linking of several percent. Then, a desired molding is formed by using the irradiated copolymer powder or pellet in a suitable manner such as the extrusion molding, injection molding, or the like, and the molding is again irradiated with γ-rays and/or electron beam, attaining a final degree of cross-linking. This method is convenient where the noncross-linked copolymer is so soft that the resultant molding loses its original form.

In a third embodiment, the noncross-linked copolymer is formed into a sheet and the sheet is subjected to the irradiation of electron beam and/or γ-rays to such a degree as to attain a desired degree of cross-linking. Then, the cross-linked copolymer sheet is used to form a desired medical utensil by a heat fusing method. Generally, when the degree of cross-linking exceeds 50%, use of a heat fusing such as a high frequency fusing having high workability, becomes impossible. When in this embodiment it is desired to increase the degree of cross-linking, irradiating the utensil after molding once again would be sufficient.

As described above, the cross-linking degree of the cross-linked copolymer is 20 to 75%. 30 to 75% is preferable for an elastic utensil such as a tube, and 50 to 75% is preferable for a utensil having vapor non-permeation and/or high oil resistance.

A radiation source includes a γ-ray source such as cobalt 60 and an electron beam generator such as a resonance transformer type electronic ray source.

The dosage of irradiation is determined depending upon the kind of the copolymer and a desired degree of cross-linking. Generally, in the case of γ-ray irradiation, the above cross-linking degree is obtained by irradiating the copolymer by 1 to 15 Mrad, preferably 5 to 10 Mrad, in total, at the rate of 0.5 Mrad/hour. In order to attain the degree of cross-linking as mentioned above by electron beam, a total dosage of 1 to 10 Mrad at 10 Mrad/second would be sufficient if a voltage of 2 Mega electron volts is applied.

The degree of cross-linking is determined from the following equation $$\text{Degree of cross-linking (\%)} = B/A \times 100 \tag{1}$$

where A is the dry weight of the cross-linked copolymer, and B is the dry weight of the residue remaining when the cross-linked copolymer is boiled in a solvent such as xylene for about two hours. For reference, the cross-linking degree obtained when a specified dose of γ-rays is irradiated at a specified rate to the ethylene-vinyl acetate copolymer having various compositions are tabulated in Table A.

TABLE A

| Ethylene-vinyl copolymers Content (%) of vinyl acetate | Dosage rate (Mrad/hr) | Dosage (Mrad) | Gel content (%) |
|---|---|---|---|
| 15 | 0.475 | 10.5 | 54 |
| 20.5 | 0.475 | 10.5 | 55 |
| 30 | 0.475 | 10.5 | 54 |
| 15 | 0.475 | 21 | 64 |
| 20.5 | 0.475 | 21 | 62 |
| 30 | 0.475 | 21 | 55 |
| 15 | 0.475 | 31.5 | 64 |
| 20.5 | 0.475 | 31.5 | 63 |
| 30 | 0.475 | 31.5 | 54 |
| 30 | 0.545 | 4.6 | 75 |
| 26 | 0.96 | 5.4 | 75 |

The cross-linked copolymer used in the present invention does not need to contain plasticizers and yet exhibits excellent medicine resistance, acid resistance, alkali resistance, and rubber elasticity as well as good mechanical workability, gas non-permeability, and heat resistance. Further, the copolymer is stable to body fluid such as blood. Additionally, it is good in high frequency fusibility, ensuring easy working.

FIG. 1 shows a fluid supply bag which is formed by high frequency fusing the peripheral portion 11a of two cross-linked copolymer sheets 11. At one end of the bag are provided a couple of tubes 13 having caps 12 made of the cross-linked copolymer.

Figure 2:
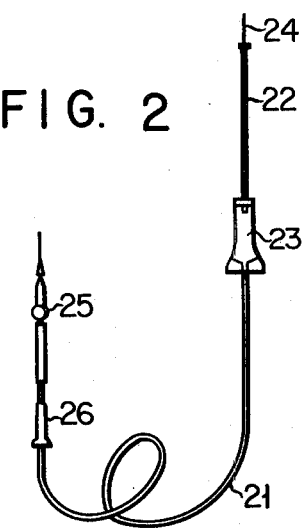
FIG. 2 shows a schematic view of a fluid supply set according to the present invention.

FIG. 2 shows a fluid supply set including two tubes 21 and 22 which are made of the cross-linked copolymer. A dripping device 23 is provided between the tubes 21 and 22. A needle 24 to be inserted into dripping liquid is connected at the top end of the tube 22. An injection needle 25 is fitted at the top end of the tube 21. A clamp 26 for regulating the flow rate of the dripping liquid is disposed on the middle way of the tube 21.

Figure 3:
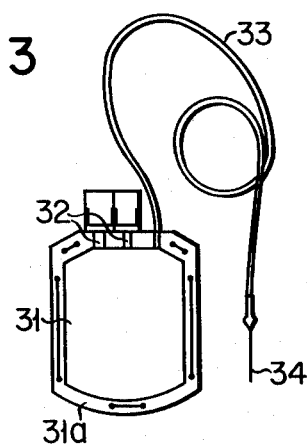
FIG. 3 shows a blood bag which is another embodiment of the present invention.

FIG. 3 shows a blood bag made of the cross-linked copolymer. The blood bag includes a bag body which is formed by high frequency fusing the peripheral edges 31a of two sheets of cross-linked copolymer and a communicating pipe 32 mounted to the main body, and a tube 33 of which the tip end is coupled with a needle 34.

Figure 4:
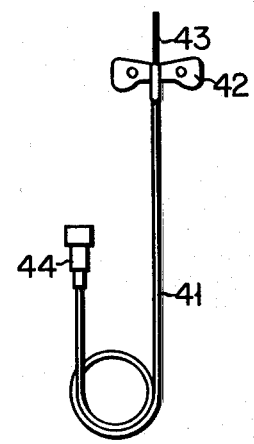
FIG. 4 shows indwelling needle device which is still another embodiment of the present invention.

FIG. 4 shows an indwelling needle device having a tube 41 made of the cross-linked copolymer. The tube 41 is provided at one end with a needle 43 having indwelling vane 42 while at the other end with a coupling means 44 for coupling with other devices.

Figure 5:
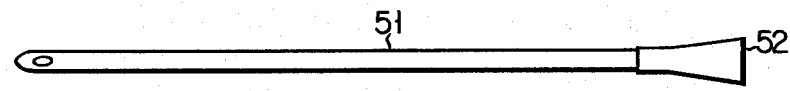
FIG. 5 shows a catheter which is the other embodiment of the present invention.

FIG. 5 shows a catheter including a tube 51 made of the cross-linked copolymer. The tube 51 is provided at one end with a connecting means 52 to be connected to a suction or exhaustion means.

The medical utensils according to the present invention include artificial organ such as an artificial kidney as well as the above-mentioned examples.

The medical utensils of the invention satisfy the standard requirements prescribed in the Pharmacopoeia of Japan, plastic containers for aqueous infusions.

The present invention will be more fully understood from the following examples.

EXAMPLE 1

Sheets, 0.4 mm thick, of ethylene-vinyl acetate copolymers each having vinyl acetate unit content as shown in Table 1 and the balance of ethylene unit were punched into a dumb-bell No. 1 sheet. The dumb-bell sheet was subjected to the irradiation of γ-rays issuing from cobalt 60 by the dosage shown in Table 1 at the rate of 0.5 Mrad/hour under nitrogen at 20° C., thus obtaining the specimens each numbered in Table 1.

TABLE 1

| Dosage | Vinyl acetate | | | | | |
|---|---|---|---|---|---|---|
| | 6% | 10% | 11% | 16% | 20% | 28% |
| 0 Mrad | 06 | 010 | 011 | 016 | 020 | 028 |
| 1 | 16 | 110 | 111 | 116 | 120 | 128 |
| 3 | 36 | 310 | 311 | 316 | 320 | 328 |
| 5 | 56 | 510 | 511 | 516 | 520 | 528 |
| 8 | 86 | 810 | 811 | 816 | 820 | 828 |
| 10 | 106 | 1010 | 1011 | 1016 | 1020 | 1028 |

Experiments shown in Tables 2 and 3 were conducted by using the specimens obtained above.

As seen from Table 2, particularly, potassium permanganate consumption is considerably reduced by the cobalt irradiation. This implies that little reductive material was included in the cross-linked copolymer.

The results shown in Table 3 shows that the cross-linked copolymer is suitable for medical utensils inter alia, fluid supply bags, tubes or fluid supply sets, fluid supply tubes, etc.

The distinguishable effects resulting from the cobalt irradiation are the reduction of the swellingness by, and of solubility into, soy bean oil, so that the cross-linked copolymer becomes applicable to nutritive fluid supply sets or bags.

TABLE 2

| Testing Items | Specimen No. | | | | | | | | | | | Remarks |
|---|---|---|---|---|---|---|---|---|---|---|---|---|
| | 06 | 010 | 020 | 56 | 510 | 520 | 528 | 106 | 1010 | 1020 | 1028 | |
| Potassium permanganate consumption (0.01N, ml) | 0.39 | 0.35 | 0.39 | 0.11 | 0.11 | 0.09 | 0.09 | 0.09 | 0.09 | 0.09 | 0.08 | Note 1 |
| Change of pH (ΔpH) | 0.18 | 0.18 | 0.19 | 0.13 | 0.13 | 0.14 | 0.13 | 0.12 | 0.12 | 0.11 | 0.12 | |
| Chloride | Appropriate | Appropriate | Appropriate | Appropriate | Appropriate | Appropriate | Appropriate | Appropriate | Appropriate | Appropriate | Appropriate | |
| Ammonia, Sulfate | Appropriate | Appropriate | Appropriate | Appropriate | Appropriate | Appropriate | Appropriate | Appropriate | Appropriate | Appropriate | Appropriate | |
| Heavy metal, Evaporation (mg) | 0.4 | 0.3 | 0.4 | 0.2 | 0.2 | 0.2 | 0.2 | 0.09 | 0.08 | 0.08 | 0.08 | |
| Coloration | None | None | None | None | None | None | None | Light brown | Light brown | Light brown | Light brown | |
| Celluar virulence | Minus | Minus | Minus | Minus | Minus | Minus | Minus | Minus | Minus | Minus | Minus | Note 2 |
| Hemolytic virulence | " | " | " | " | " | " | " | " | " | " | " | Note 3 |
| Microbe permeability | " | " | " | " | " | " | " | " | " | " | " | |

TABLE 2-continued

| Testing Items | Specimen No. | | | | | | | | | | | Remarks |
|---|---|---|---|---|---|---|---|---|---|---|---|---|
| | 06 | 010 | 020 | 56 | 510 | 520 | 528 | 106 | 1010 | 1020 | 1028 | |
| Acute virulence | " | " | " | " | " | " | " | " | " | " | " | |
| Subcutaneous reaction | " | " | " | " | " | " | " | " | " | " | " | |
| Pyrexia material | " | " | " | " | " | " | " | " | " | " | " | |
| Transplantation test | " | " | " | " | " | " | " | " | " | " | " | |

Note 1: Distilled water for solvent injection; at 121° C. for 60 minutes.
Note 2: 1 g/3 ml MEM culture medium at 121° C. for 20 minutes.
Note 3: 121° C. for 20 minutes, autoclave extraction, after 24 hours.

TABLE 3

Weight Reduction (%)

| | Specimen No. | | | | | |
|---|---|---|---|---|---|---|
| | 011 | | 511 | | 520 | |
| | Immersed days | | | | | |
| Testing Item | After 3 days | After 12 days | After 3 days | After 12 days | After 3 days | After 12 days |
| 99.5% ethyl alcohol | 0.42 | 0.49 | 0.20 | 0.20 | 0.20 | 0.20 |
| 43% glycerin | 0.02 | 0.04 | 0.01 | 0.01 | 0.01 | 0.01 |
| 50% polyethylene glycol | 0.03 | 0.05 | 0.01 | 0.01 | 0.01 | 0.01 |
| 10% intralipit | 0.15 | 0.23 | 0.02 | 0.02 | 0.02 | 0.02 |
| Soy bean oil | 8.75 | 11.23 | 0.21 | 0.20 | 0.21 | 0.20 |

The heat resistance depends on the composition of the ethylene-vinyl acetate copolymer. The deformation temperature for this copolymer is 70° C. for 28% of vinyl acetate content, 86° C. for 16% of vinyl acetate content, and 89° C. for 11% of vinyl acetate content. The cross-linked copolymer having 6 to 28% of vinyl acetate content, as prepared from irradiation thereto of a dose of 1 to 10 Mrad is durable to the condition of autoclave sterilization that it is placed in vapor at 121° C. for 60 minutes. Even if the dosage exceeds 10 Mrad, the heat resistance is further enhanced, but it adversely affects the high frequency sealing characteristic.

Good results also were obtained in the absorption of vitamin, the non-permeability of water vapor, residual ethylene oxide gas after sterilization by ethylene oxide gas, and the like. Most of these tests were conducted in accordance with the Pharmacopoeia of Japan, plastic containers for infusion.

Further, blood bags, catheters, fluid supply sets (these are typical goods sold with trade names (Teruflex, Sufud and Terufusion by Terumo Co., Ltd., Japan), were formed from specimens numbered 020, 520, 820 and 1020 in the Example 1. These were tested for the function as of desired medical utensils. The specimen 020 was undurable to the condition of autoclave sterilization, but it exhibited no abnormality when other tests were performed. The transparency was almost equal for the specimens 520, 820 and 1020. With respect to the flexibility, the specimen 520 is superior to the specimen 1020 and thus the former is suitable for soft medical utensils, and the latter is suitable for the catheter with relative large diameter.

EXAMPLE 2

The specimen used was ethylene-vinyl acetate-vinyl chloride copolymer (R-5L made by Japan Geon Co., Ltd.). The composition of the copolymer was ethylene 35%, vinyl chloride 50%, and vinyl acetate 15%. For irradiation, cobalt 60 was used with the dose of 5 Mrad and 10 Mrad. Testing items are an eluted material test (Table 4), a biological assay (Table 5), and heat resistance and high frequency sealingness (Table 6).

TABLE 4

(Eluted Material Test)

| | Specimen Number | | |
|---|---|---|---|
| | R-0 | R-5 | R-10 |
| Dosage (Mrad) | 0 | 5 | 10 |
| Nature | Transparency | Transparency | Transparency |
| Foaming | Appropriate | Appropriate | Appropriate |
| Change of pH | 0.48 | 0.08 | 0.08 |
| Chloride, Acetate, Microcosmic salt, Salt, Ammonium | Appropriate | Appropriate | Appropriate |
| Evaporated remains | 0 | 0 | 0 |
| Potassium permanganete consumption ml | 0.10 | 0.02 | 0.02 |

TABLE 5

(Biological Assay)

| | Specimen Number | | |
|---|---|---|---|
| | R-0 | R-5 | R-10 |
| Celluar virulence | — | — | — |
| Hemolytic virulence | | | |
| After 1 hour | + | — | — |
| After 4 hours | + | — | — |
| After 24 hours | + | — | — |
| Acute virulence | + | — | — |
| Microbe permeability | + | — | — |
| Subcutaneous reaction | + | — | — |
| Pyrexia | + | — | — |
| Transplantation test | + | — | — |

TABLE 6

(Heat Resistance)

| | Specimen Number | | |
|---|---|---|---|
| | R-0 | R-5 | R-10 |
| Heat resistance (temperature transformation) | <75° C. | <121° C. | <125° C. |
| Autoclave sterilization, 121° C., 60 minutes | Impossible | Possible | Possible |
| High frequency sealingness | Possible | Possible | Possible |

The results of the tests using ethylene-vinyl acetate-vinyl chloride copolymer show many useful improvements: The heat resistance is improved due to the radioactive irradiation; Consumption of potassium permanganate is considerably improved; Hemolytic virulence which is essential to the medical utensils is improved.

EXAMPLE 3

Using benzoyl peroxide as an initiator, ethylene (80%) and butyl acrylate (20%) were radical-polymerized at 50° C. for 8 hours in a stainless autoclave. The ethylene-butyl acrylate copolymer obtained is formed into a sheet (dumb-bell No. 1 with 0.4 mm thickness) which was in turn irradiated with the cobalt 60. The irradiation condition was the same as in Example 1.

The results are shown in Table 7 (eluted material test), Table 8 (biological assay) and Table 9 (heat resistance).

TABLE 7

| | Specimen Number | | |
|---|---|---|---|
| | B-0 | B-5 | B-10 |
| Dosage (Mrad) | 0 | 5 | 10 |
| Nature | Transparency | Transparency | Transparency |
| Foaming | Appropriate | Appropriate | Appropriate |
| Change of pH | 0.59 | 0.10 | 0.10 |
| Chloride, Acetate, Microcosmic salt, Ammonia | Appropriate | Appropriate | Appropriate |
| Evaporated remains | 0.01 | 0.01 | 0.01 |
| UV absorption | Appropriate | Appropriate | Appropriate |

TABLE 8

| | Specimen Number | | |
|---|---|---|---|
| | B-0 | B-5 | R-10 |
| Celluar virulence | + | − | − |
| Hemolytic Virulence | | | |
| After 1 hour | + | − | − |
| After 4 hours | + | − | − |
| After 24 hours | + | − | − |
| Acute virulence | + | − | − |
| Microbe permeability | + | − | − |
| Subcutaneous reaction | + | − | − |
| Pyrexia | + | − | − |
| Transplantation test | + | − | − |

TABLE 9

| Specimen | Heat resistance | High frequency Sealingness |
|---|---|---|
| B-0 | <60° C. | Possible |
| B-5 | <115° C. | Possible |
| B-10 | <119° C. | Possible |

These tables show that the use of ethylene-butyl acrylate copolymer improves the heat resistance provided by the radioactive radiation and is suitable for the material of the medical utensils.

EXAMPLE 4

A fluid supply container, a blood supply container, a nutritive fluid supply container and a urine bag according to the present invention were prepared in the following manner. The ethylene-vinyl acetate copolymer including vinyl acetate 17, 20 and 25% was extrusion-molded to form sheets with thicknesses 0.1, 0.15, 0.2, 0.25 and 0.4 mm. Two sheets with the same thickness were superposed and fused at the periphery except about 1 cm opening by high frequency sealing to form a rectangular planer container of 10 cm×10 cm. The container was placed in a polyethylene bag and then was nitrogen-substituted. Following this, it was irradiated with electron beam by 8 Mrad to cross-link it. For testing the evaporation of solvent for fluid of supply, anti-coagulating agent for fluid supply, nutritive fluid of supply, urine, or the like, water, 80 ml, was poured in the thus prepared container and is opening is sealed by high frequency sealing. Two vinyl chloride container A and B with the same shape as of the ethylene-vinyl acetate container were prepared containing 80 ml of water.

Figure 6:
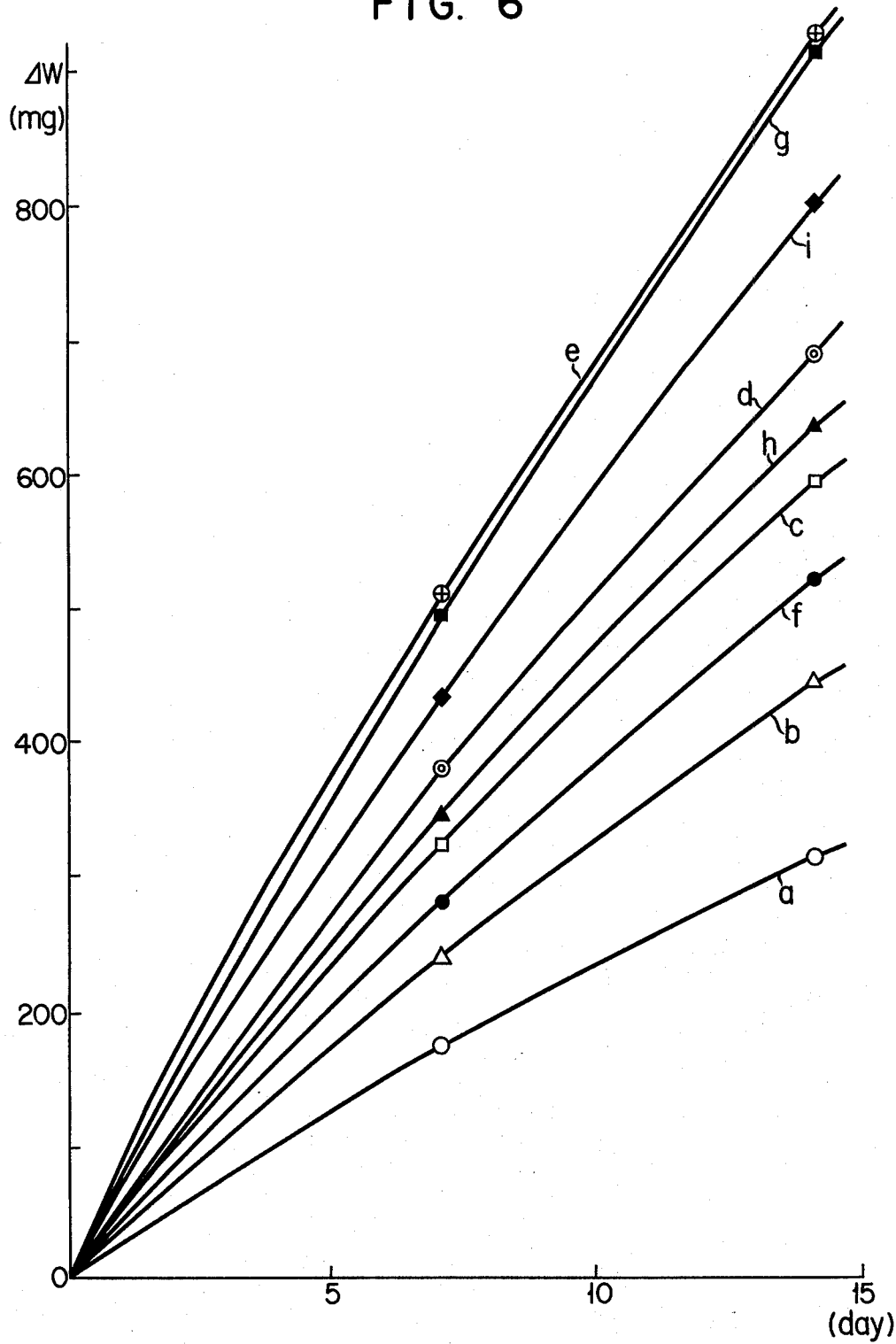
FIG. 6 shows graphs comparatively illustrating water vapor permeability characteristic curves of the medical utensils according to the present invention and a conventional one.

The vapor permeability of these containers were measured by placing the containers in an atmosphere at 20° C. and 65% of absolute humidity of 0, 7 and 14 days and weighing them. The results are shown in FIG. 6. In the figure the curves a to j relates to the cases shown in Table 10 below.

TABLE 10

| Curves | Vinyl acetate content (%) | Thickness |
|---|---|---|
| a | 17 | 0.4 |
| b | 17 | 0.25 |
| c | 17 | 0.2 |
| d | 17 | 0.15 |
| e | 17 | 0.1 |
| f | 20 | 0.4 |
| g | 25 | 0.4 |
| h | Container A | 0.4 |
| i | Container B | 0.4 |

The container of ethylene-vinyl acetate copolymer with vinyl acetate content of 17 to 20% was superior in the water vapor permeability to the conventional vinyl acetate container for blood bag A (thickness 0.4 mm) and the vinyl chloride container B for fluid supply bag (0.4 mm in thickness).

It should be noted that the container of ethylene-vinyl acetate including vinyl acetate of 17% was superior to the conventional ones in the vapor permeability, even if the thickness of it is one and half of that of the conventional ones. Further, the result show that the lower the content of the vinyl acetate, the better vapor non-permeability. Additionally, the cross-linked ethylene-vinyl acetate copolymer is filled with water and sterilized under a high pressure vapor. Breakage and solution of the container and elution of the monomer into water were not observed.

With medicine proof, microbe permeability, acute virulence, and pirexia material tests, the ethylene-vinyl acetate copolymer exhibits much the same results as of the Example 1.

What we claim is:

1. A medical bag containing liquid medicine comprising:

a flexible bag body which is durable to autoclave sterilization at a temperature as high as 121° C. formed of a copolymer cross-linked by electron beam irradiation of a total dose of 5 to 15 Mrad and having the degree of cross-linking of 50 to 75% such that said bag body withstands high vapor pressure sterilization without deformation, said copolymer having units represented by the formulas:

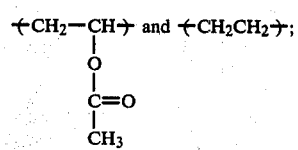

and a liquid medicine contained in said bag body.

2. A medical bag according to claim 1, wherein said bag body is provided by a pair of sheets formed of said cross-linked copolymer.

3. A medical bag according to claim 2, wherein said sheets have a thickness of 0.1 to 0.4 mm.

4. A medical bag according to claim 1, wherein said copolymer has a weight average molecular weight of about 10,000 to 250,000.

5. A medical bag according to claim 1, wherein said bag body withstands the attack by said liquid medicine.

6. A medical bag according to claim 5, wherein said bag body exhibits low vapor permeability.

7. A medical bag containing liquid medicine comprising:

a flexible bag body which is durable to autoclave sterilization at a temperature as high as 121° C. formed of a copolymer having units represented by the formulas:

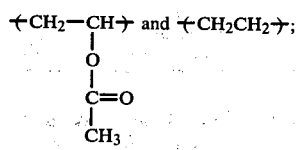

and a liquid medicine contained in said bag body, wherein said bag body is prepared by heat-fusing peripheral portions of a bag molding prepared from said copolymer, and irradiating said bag molding with electron beam at a total dose of 5 to 15 Mrad to attain the degree of cross-linking of 50 to 75% in said copolymer forming said bag molding, thereby providing said bag body.

8. A medical bag according to claim 7, wherein the bag molding has a thickness of 0.1 to 0.4 mm.

9. A medical bag according to claim 7, wherein said copolymer has a weight average molecular weight of about 10,000 to 250,000.

10. A medical bag according to claim 7, wherein said bag body withstands attack by said liquid medicine.

11. A medical bag according to claim 7, wherein said bag body exhibits low vapor permeability.

12. A medical bag containing liquid medicine comprising:

a flexible bag body formed of an ethylene-vinyl acetate copolymer of from 15 to 30% vinyl acetate units and 70 to 85% ethylene units cross-linked by electron beam irradiation at a total dose of 5 to 15 Mrad and having a degree of cross-linking of about 50 to 75% such that said bag body is durable to autoclave sterilization at a temperature as high as 121° C.; and a liquid medicine contained in said bag body.

13. A medical bag according to claim 8, wherein the ethylene-vinyl acetate copolymer contains from about 17 to 20% of vinyl acetate units with the remainder being ethylene units.

* * * * *